United States Patent [19]

Imperato et al.

[11] Patent Number: 5,039,680
[45] Date of Patent: Aug. 13, 1991

[54] NEW USE OF 5HT-3 ANTAGONISTS IN PREVENTING OR REDUCING DEPENDENCY ON DEPENDENCY-INDUCING AGENTS

[75] Inventors: Assunta Imperato, Rome, Italy; Dietmar Römer, Allschwil, Switzerland

[73] Assignee: Sandoz Ltd., Basel, Switzerland

[21] Appl. No.: 467,598

[22] Filed: Jan. 19, 1990

Related U.S. Application Data

[63] Continuation of Ser. No. 217,016, Jul. 8, 1988, abandoned.

[30] Foreign Application Priority Data

Jul. 11, 1987 [DE] Fed. Rep. of Germany ....... 3722959
Oct. 22, 1987 [DE] Fed. Rep. of Germany ....... 3735719
Nov. 19, 1987 [CH] Switzerland ....................... 04510/87

[51] Int. Cl.$^5$ ...................... A01N 43/42; A01N 43/50
[52] U.S. Cl. .................................. 514/304; 514/397; 514/810; 514/812; 514/813
[58] Field of Search ............... 514/304, 397, 810, 812, 514/813

[56] References Cited

U.S. PATENT DOCUMENTS 4,847,281 7/1989 Tyers ................................. 514/397

Primary Examiner—Stanley J. Friedman
Assistant Examiner—T. J. Criares
Attorney, Agent, or Firm—Gerald D. Sharkin; Robert S. Honor; Joseph J. Borovian

[57] ABSTRACT

The invention provides use of a 5HT-3 antagonist in the manufacture of a medicament suitable for the prevention or reduction of dependence on a dependence-inducing agent.

7 Claims, No Drawings

NEW USE OF 5HT-3 ANTAGONISTS IN PREVENTING OR REDUCING DEPENDENCY ON DEPENDENCY-INDUCING AGENTS

This is a continuation of application Ser. No. 07/217,016, filed July 8, 1988, now abandoned.

This invention relates to a new use of 5HT-3 antagonists.

These compounds are also referred to hereinafter as compounds of the invention.

5HT-3 antagonists are a class of compounds which block 5HT-3 receptors. Examples include compounds disclosed in Belgian patents Nos. 897117, 900425 and 901274. These compounds are described therein as being 5HT-3 receptor antagonists or serotonin M receptor antagonists (serotonin M receptors have been reclassified as 5HT-3 receptors).

Other classes of the compounds of the invention are known from e.g. European patent publications Nos. 13138A, 250444A, and 214772A and British Patent publication No. 2153821.

5HT-3 antagonist from various sources have been published for a wide variety of uses, for example for the treatment of migraine, arrhythmia, serotonin-induced gastro-intestinal disorders, including emesis induced by anti-cancer agents, anxiety, stress-related psychiatric disorders, lung embolism, rhinitis or serotonin-induced nasal disorders, and for increasing vigilance.

We have surprisingly found that the compounds of the invention act within the central nervous system to antagonize dopamine release, e.g. in the nucleus accumbens, induced by dependence-inducing agents such as psychostimulants, opiates, alcohol or nicotine, as indicated by the pharmacological tests as described hereinafter. 5HT-3 antagonists are therefore useful in preventing and reducing the development of dependency on such dependency-inducing agents, independent of, e.g. an anxiolytic effect.

This finding opens up a completely new method of treating dependence on drugs, nicotine, alcohol and the like. Such psychological and physical dependence on agents such as opiates, alcohol and other CNS depressants, psychostimulants, and nicotine has become a serious medical and social problem.

We have found, using the microdialysis technique in freely moving awake rats (A. Imperato et al., J. Pharmac. and Exp. Therap. (1986), 239, 219–228 and G. Di Chiara and A. Imperato, Preferential stimulation of dopamine release in the nucleus accumbens by opiates, alcohol and barbiturates: studies with transcerebral dialysis in freely moving rats in Neurotransmitter interactions in the basal ganglia, Edited by C. Sandler, B. Feuerstein and B. Scatton, Raven Press, New York, 1987, p. 171), that dependency-inducing agents induce at low parenteral doses, e.g. from about 1 to about 5 mg/kg s.c. in the case of morphine, 0.6 mg/kg s.c. in the case of nicotine, and about 5 mg/kg i.p. in the case of ethanol, a stimulation of dopamine release and dopamine metabolism in the nucleus accumbens (a major target of the limbic system), but not in the nucleus caudatus. Behavioural effects, e.g. stereotypies (catalepsy) in the case of morphine, locomotion in the case of nicotine and hypnosis in the case of ethanol, correlate in time with the stimulation of dopamine release.

In the above test administration of 5HT-3 antagonists is made subcutaneously at a dose of from about 50 to about 5000, e.g. 200 to 1000, microgram/kg s.c. about 75 minutes before administration of a dependence-inducing agent such as morphine at 1 mg/kg s.c., nicotine at 0.6 mg/kg s.c., or ethanol at 2.5 mg/kg i.p. An inhibition of the drug-induced increase of dopamine release in the nucleus accumbens together with an inhibition of its behavioral effects is observed.

Additionally, the 5HT-3 antagonist may be administered through chronic, indwelling cannulas implanted bilaterally into the ventral tegmental area (VTA) (area of origin of the mesolimbic dopaminergic neurons) of the mid-brain of the rat. Typical coordinates are (from König and Klippel Atlas): $A = -5.2 \pm 1.0$ taken from the bregma; $V = -8.5$ taken from the dura). Doses used are e.g. from 1 to 10 microgram in 0.5 microliters of saline. Administration is effected about 40 minutes after injection of morphine or other dependency-inducing agent. An antagonism of the normal increase of dopamine release is observed.

These 5HT-3 antagonists may be preferably chosen from the following compounds:

Indol-3-yl-carboxylic acid-endo-8-methyl-8-aza-bicyclo[3,2,1]-oct-3-yl-ester (also known as ICS 205-930) [hereinafter called compound E];

benzo[b]thiophen-3-yl-carboxylic acid-endo-9-methyl-azabicyclo-[3,3,1]non-3-yl-ester [hereinafter called compound F];

5-fluoro-1-methyl-indol-3-yl-carboxylic acid-endo-9-methyl-9-aza-bicyclo[3,3,1]non-3-yl-ester [hereinafter called compound G];

1,2,3,9-tetrahydro-9-methyl-3-[(2-methyl-1H-imidazol-1-yl)-methyl]-4H-carbazol-4-one (also known as GR 38032F) [hereinafter called compound H];

1-methyl-indazol-3-yl-carboxylic acid-9-methyl-9-aza-bicyclo-[3,3,1]-non-3α-yl-amide (also known as BRL 43694) [hereinafter called compound I];

endo-4-amino-5-chloro-2-methoxy-N-(1-azabicyclo[3,3,1]non-4-yl)-benzamide (also known as BRL 24924) [hereinafter called compound J].

3-[5-methyl-1H-imidazol-4-yl]-1-(1-methyl-1H-indol-3-yl)-1-propanone and the compound GR-68755.

Compound E is preferred in particular.

In the VTA rat test described above the stimulation of dopamine release induced by 1.0 mg/kg s.c. morphine is lowered within 20 minutes from +65% (calculated on the basal values) to −30% upon injection of 10 micrograms of compound E.

It was similarly established that the stimulation of dopamine release induced by systemic ethanol or nicotine is reduced by compound E to approximately basal values, when administered into the VTA region.

Thus, e.g. the stimulation of dopamine release which was induced by 2.5 g/kg i.p. ethanol is lowered within 20 minutes from +75% (calculated on the basal values) to 17% upon injection of 2.5 micrograms of compound E.

Furthermore, e.g. the stimulation of dopamine release induced by 0.6 mg/kg s.c. nicotine is lowered within 20 minutes from +75% (calculated on the basal values) to −18% upon injection of 2.5 micrograms of compound E.

In the above test, compound E shows a threshold dose at 50 microgram/kg s.c. 100 microgram/kg s.c. totally antagonizes dopamine release and metabolism.

Any of compounds F,G,H,I and J can be tested in the above trials, and similar results are obtained.

Further psychostimulants, such as opiates, may be used in analogous manner, whereby again similar results are obtained with compounds E,F,G,H and I, e.g. using 200 ug/kg s.c. of compound E.

Compound E, when injected at doses of from 25 to 1000 microgram/kg s.c. does not significantly affect the spontaneous release or metabolism of dopamine in freely moving rats.

Compound E does not act directly at the nucleus accumbens as indicated by an insignificant influence on or blocking of the spontaneous release of dopamine after 1.0 mg/kg s.c. morphine upon two hours perfusion with compound E at a concentration of $10^{-4}$M in the nucleus accumbens.

The effects of a 5HT-3 antagonist in preventing or reducing the development of dependency on a dependency-inducing agent is observed in rhesus monkeys, wherein the antagonist is administered in a programmed manner to monkeys which can self-administer themselves with morphine over 4 weeks.

Monkeys are tested for their physical dependence liability according to the test described in R. W. Foote et al., Life Sciences 1988, 42, 137–152. Drug naive monkeys receive by infusion from 1 to 10 mg/kg e.g. 2 mg/kg daily, of the 5HT-3 antagonist by programmed administration, e.g. 48 infusions per day, and may self-administer morphine (100 microgram/kg per infusion per administration), also intravenously from the 2nd week. The trial lasts for 6 weeks. A typical dose of morphine that is self-administered by animals receiving 5-HT-3 antagonist treatment is 10 to 12 mg/kg per day. This is surprisingly lower than the typical dose self-administered by control animals (about 50% lower).

There is then a wash-out period of 8 weeks. The monkeys are then allowed to self-administer morphine over 2 weeks. The dose of morphine that is self-administered by animals formerly exposed to 5-HT-3 antagonists is lower than that self-administered by control animals.

In the above test, compound E is administered at 2 mg/kg daily. Typical results show that over four weeks the morphine self-administered dose increases from 7 mg to 16 milligrams per day when no compound E is administered. After a wash out period compound E is administered by programmed administration and morphine by self-administration. The morphine dose starts at 2 mg/kg per day and increases to only 5 mg/kg per day over 4 weeks.

5HT-3 antagonists are thus indicated for use in preventing or reducing the rewarding (positive reinforcement) action of dependency-inducing agents.

The compounds of the invention are therefore useful in preventing or reducing dependency on dependency-inducing agents.

For these indications, the appropriate dosage will, of course, vary depending upon, for example, the compound of the invention employed, the host, the mode of administration and the nature and severity of the condition being treated. However, in general, satisfactory results are indicated to be obtained at daily dosages from about 0.1 microgram/kg to about 0.5 mg/kg animal body weight. In humans, an indicated daily dosage is in the range from about 0.05 mg to about 20 mg of a compound of the invention conveniently administered, for example, in divided doses every 4 to 6 hours or up to four times a day.

Dosaging already known, e.g. for administration against cis-platin induced emesis (e.g. oral pharmaceutical compositions containing 4 mg of compound H have been published as being effective in clinical trials for cis-platin induced emesis) may be used in the method of the invention. Particularly interesting results may be obtained with daily doses which are significantly lower than those administered for known indications. In general, compound E is administered in doses of between 0.1 and 10 milligrams daily e.g. 5 mg p.o. Compounds F–I are effective at daily doses of ca. 0.05 to 4.0 milligrams. The 5HT-3 antagonist may be administered using a dosage schedule, e.g. every 4 to 6 hours, or it may be administered to conform to the requirements of the patient. The preferred compound E is administered in single doses of ca. 0.5 to 2.5 milligrams 2 to 4 times daily, preferably 0.5 to 1 milligram 2 to 3 times daily.

A single oral dose of ca. 0.5 to 1 milligram of a 5HT-3 antagonist is normally sufficient to attain a satisfactory result.

The dependence-inducing agent may be administered in normal doses. Thus for example morphine may be administered e.g. at a dose of 10 mg s.c. or i.p. to induce an analgesic effect, e.g. in hospitalized patients.

The 5-HT-3 antagonists may be administered after administration of the dependence-inducing agent. Preferably however, they are administered concomitantly or before administration of the dependence inducing agent.

The method of the invention is of particular value for patients who have already been addicted and have been treated for withdrawal symptoms, so that administration of a 5HT-3 antagonist prevents development of renewal dependence, or prevents relapse into addiction.

The present invention accordingly provides:

a) Use of a 5HT-3 antagonist in the manufacture of a medicament suitable for the prevention or reduction of dependence on a dependence-inducing agent, b) Use of a 5HT-3 antagonist for the prevention or reduction of dependence on a dependence-inducing agent, c) A method of preventing or reducing dependency on a dependency-inducing agent in a subject which comprises administering a 5HT-3 antagonist to a subject in need of such treatment, d) A method of reducing addiction to smoking or alcohol which comprises administering a 5HT-3 antagonist to a subject in need of such treatment, e) A pharmaceutical composition comprising a 5HT-3 antagonist and a dependency-inducing amount of a dependency-inducing agent, f) A composition comprising a 5HT-3 antagonist and nicotine, and/or g) An oral unit dosage pharmaceutical composition comprising from 0.5 to 1 milligram of a 5HT-3 antagonist.

The invention also provides:

i) Use of a mono- or bicyclic-, carbocyclic or heterocyclic, carboxylic acid ester or amide of a nitrogen-containing alcohol or amine, or an acid addition salt thereof or a quaternary ammonium salt thereof, in the manufacture of a medicament suitable for the prevention of, or reduction of dependency on, or for treatment after a period of withdrawal, to avoid renewed dependency on, a psychostimulant, an opiate, or alcohol or nicotine, or ii) use of mono- or bicyclic, carbocyclic or heterocyclic, carboxylic acid ester or amide of a nitrogen-containing alcohol or amine or a imidazolyl-carbazole, or an acid addition salt thereof or a quaternary ammonium salt thereof, in the manufacture of a medicament suitable for the treatment of addiction to a psychostimulant or to prevent or discontinue the need for the psychostimulant.

The invention is also of value for the prevention of renewed dependency on a dependency-inducing agent after a period of withdrawal from said dependency-inducing agent.

Preferably the compounds of the invention are selective 5HT-3 antagonists in that they do not block significantly 5HT-1 or 5HT-2 receptors. A group of compounds of the invention are those which do not show affinity for alpha-1, alpha-2, beta-1 and/or beta-2 adrenoreceptors, $D_1$ and/or $D_2$ dopaminergic receptors and/or benzodiazepine receptors.

Compound E has an affinity for all 3 types of 5HT-3 receptors (e.g. as characterized by their action on the vagus, ileum and heart). Compounds of the invention may be selective for any one of these receptors.

Conveniently the 5HT-3 antagonist is a mono or bicyclic carbocylic, or heterocyclic carboxylic acid ester or amide, or an imidazolyl carbazole, e.g. a mono- or bicyclic-carbocyclic or heterocyclic, carboxylic acid ester or amide of a nitrogen-containing alcohol or amine, or a acid addition salt thereof or a quaternary ammonium salt thereof.

In one group of compounds the 5-HT-3 antagonist is other than an imidazolyl carbazole.

In another group of compounds the 5-HT-3 antagonist is other than 1,2,3,9-tetrahydro-9-methyl-3-[(2-methyl-1H-imidazolyl-1-yl)methyl]-4H-carbazol-4-one.

In a further group of compounds the 5HT-3 antagonist is a bicyclic carbocyclic or heterocyclic carboxylic acid ester or amide.

In a yet further group of compounds the 5HT-3 antagonist has an imidazolyl group.

One group of compounds comprises compounds of formula I

A—B—C—D    I wherein A is a group of formula

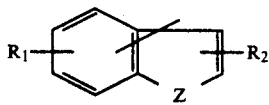  (II)

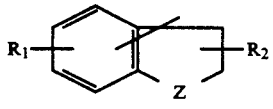  (IIa)

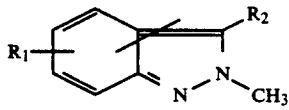  (IIb)

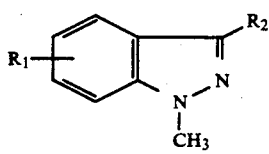  (IIc)

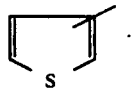  (IId)

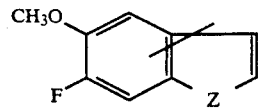  (IIe)

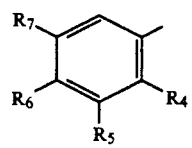  (III)

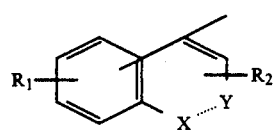  (IV)

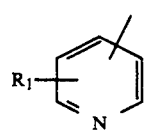  (V)

wherein the free valence is attached to either fused ring in formula II, IIa, IIb, IIe or IV, X—Y is —CH=CH—, —O=CH$_2$—, or —N=CH—, Z is —CH$_2$—, —NR$_3$—, —O— or —S—, $R_1$ and $R_2$ are independently hydrogen, halogen, ($C_{1-4}$)alkyl, ($C_{1-4}$)alkoxy, hydroxy, amino, ($C_{1-4}$)alkylamino, di($C_{1-4}$)alkylamino, mercapto or ($C_{1-4}$)alkylthio, $R_3$ is hydrogen, ($C_{1-4}$)alkyl, acyl, ($C_{3-5}$)alkenyl, aryl or arylalkyl, and $R_4$ to $R_7$ are, independently, hydrogen, amino, nitro, ($C_{1-4}$)alkylamino, di($C_{1-4}$)alkylamino, halogen, ($C_{1-4}$)alkoxy, ($C_{1-4}$)alkyl, ($C_{1-4}$)alkanoylamino, pyrrolyl, sulfamoyl, or carbamoyl, B is —CO— or —SO$_2$—, C is —O— or —NH— or a bond, and D is a group of formula

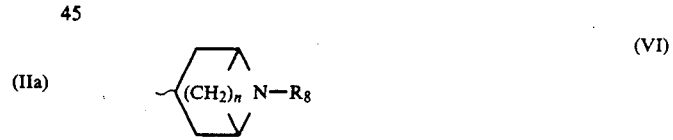  (VI)

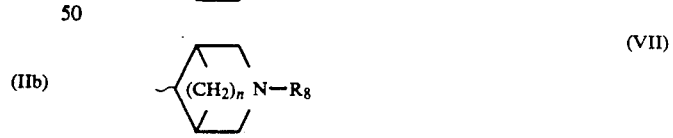  (VII)

wherein n is 2, 3 or 4

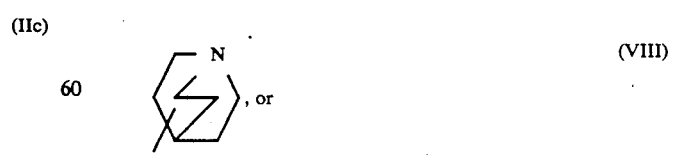  (VIII)

, or

  (IX)

wherein R₈ is hydrogen, (C₁₋₇)alkyl, (C₃₋₅)alkenyl or aralkyl, and in formula VIII the bond is in position 3 or 4, when B is CO, additionally D may be a group of formula

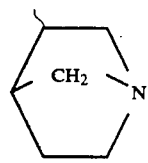 (X)

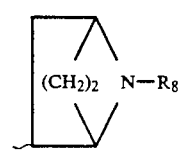 (XI)

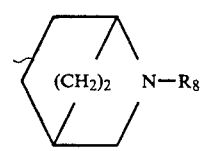 (XII)

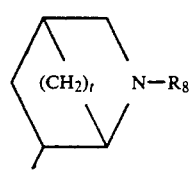 (XIII)

wherein t is 1 or 2, and R₈ is as defined above.

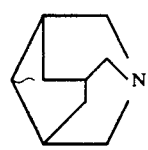 (XIV)

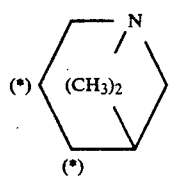 (XV)

wherein the bond is in the position 3 (*) or 4 [*],

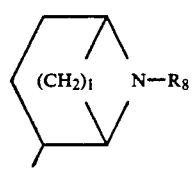 (XVI)

wherein l is 2 or 3,

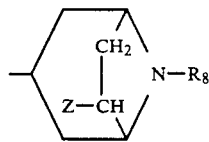 (XVII)

wherein Z is (C₁₋₄)alkoxy.

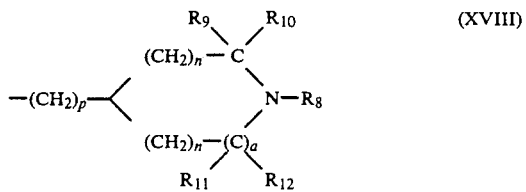 (XVIII)

wherein
R₉ to R₁₂ are independently hydrogen or (C₁₋₄)alkyl,
m is 0, 1 or 2 and
n, o, p independently are 0 or 1,

 (XIX)

wherein
q is 2 or 3,
R₁₃ and R₁₄ independently are (C₁₋₄)alkyl,

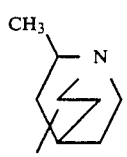 (XX)

wherein the bond is in position 3 or 4,

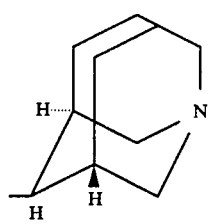 (XXI)

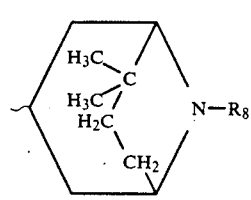 (XXII)

(XXIII)

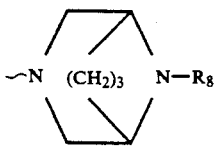
(XXIVa)

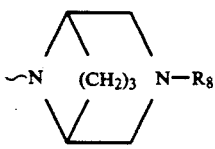
(XXIVb)

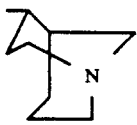
(XXV)

wherein $R_8$ is as defined above, in free base form, acid addition salt form or quaternary ammonium salt form, or a compound of formula Ia

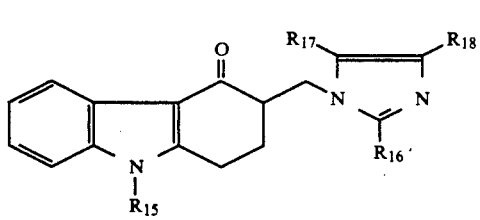
(Ia)

wherein $R_{15}$ is hydrogen, $(C_{1-10})$alkyl, $(C_{3-9})$cycloalkyl, $(C_{3-6})$alkenyl, phenyl or phenyl$(C_{1-3})$alkyl and one of the groups $R_{16}$, $R_{17}$ or $R_{18}$ is hydrogen, $(C_{1-6})$alkyl, $(C_{3-7})$cycloalkyl, $(C_{2-6})$alkenyl or phenyl$(C_{1-3})$alkyl, and the others independently are hydrogen, or $(C_{1-4})$alkyl, e.g. the compounds E to J mentioned above.

The compounds of the invention are of particular value for psychostimulant agents including cocaine, amphetamine, methamphetamine, dextroamphetamine, pemoline and pharmaceutically acceptable acid addition salts thereof such as the phosphate, sulphate and 4-chlorophenoxyacetate, opiates, e.g. morphine, as well as for nicotine and alcohol.

The 5HT-3 antagonist used in the present invention may be used in free base form or, if appropriate, in the form of a pharmaceutically acceptable salt form, for example in the form of the hydrochloride or as a quaternary ammonium salt form. In general, the effects of such salt forms lie in the same order as those of the corresponding free forms.

The compounds of the invention may be administered orally or parenterally as such, or mixed with conventional pharmaceutical carriers. They may be administered orally in the form of tablets, dispersible powders, granules, capsules, syrups and elixirs, and parenterally in the form of solutions, e.g. a sterile injectable aqueous solution. Tablets may contain the active constituents mixed with conventional, pharmaceutically acceptable excipients, e.g. inert diluents and granulating agents which disintegrate into their components and form oils. In order to extend the disintegration and absorption in the gastro-intestinal tract, and thus to achieve effectiveness over a longer period, the tablets may be coated by known methods. In a similar way, suspensions, syrups and elixirs may contain the active constituents mixed with one of the conventional excipients which are used in the production of such compositions. Capsules may contain the compounds of the invention alone or in a mixture with an inert solid diluent. Injectable compositions are formulated by known methods. These pharmaceutical preparations may contain up to ca. 90% of active constituents in combination with the carrier or assistants.

Tablets having a diameter of 6 mm, of the following composition, may be produced by known methods and are suitable for the prevention or reduction of dependency on narcotics.

| | |
|---|---|
| Compound E | 0.500 mg |
| disodium salt of ethylene- diaminetetraacetic acid 2H₂O | 0.325 mg |
| silicon dioxide (Aerosil 200) | 0.225 mg |
| lactose | 71.076 mg |
| magnesium stearate | 0.450 mg |
| corn starch | 11.700 mg |
| maleic acid | 0.650 mg |
| | 84.926 mg |

Or if desired the amount of hydrochloride corresponding to 0.5 compound E mg with correspondingly less lactose.

An equivalent amount of compound F,G,H,I or J may be used in place of the compound E.

Toxicity and Tolerability:

Toxicity and Tolerability studies may be effected in conventional manner with the compounds of the invention to determine the upper dosage.

Toxicity studies may be effected for example in the rat and the dog over for example 26 weeks.

For compound E over 26 weeks the no toxic effect in the dog was 5–20 mg/kg/daily p.o. For the rat it was 16 to 45 mg/kg per day p.o. In healthy human volunteers single doses up to 150 mg of compound E were well tolerated without relevant side effects. Other compounds of the invention have the same order of tolerability, and in some cases clinical tolerability results have been published.

We claim:

1. A method of avoiding renewed dependency on an opiate comprising administering to a subject in need of such treatment a therapeutically effective amount of a 5HT-3 antagonist of formula Ia:

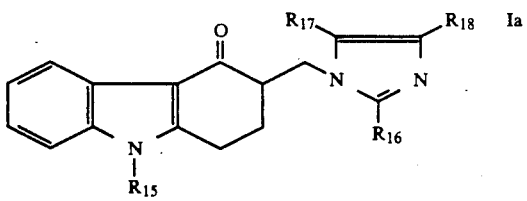
Ia wherein $R_{15}$ is hydrogen, $(C_{1-10})$alkyl, $(C_{3-9})$cycloalkyl, $(C_{3-6})$alkenyl, phenyl or phenyl$(C_{1-3})$alkyl, and one of $R_{16}$, $R_{17}$ or $R_{18}$ is hydrogen, $(C_{1-6})$alkyl, $(C_{3-7})$cycloalkyl, $(C_{2-6})$alkenyl or phenyl$(C_{1-3})$alkyl, and the other substituents are, independently, hydrogen or $(C_{1-4})$alkyl.

2. A method according to claim 1 comprising administering the compound 1,2,3,9-tetrahydro-9-methyl-3-

[(2-methyl-1H-imidazol-1-yl)-methyl]-4H-carbazol-4-one.

3. A method according to claim 1 wherein the opiate is morphine.

4. A pharmaceutical composition comprising a dependence-inducing amount of an opiate and a therapeutically effective amount of a 5HT-3 antagonist of formula Ia:

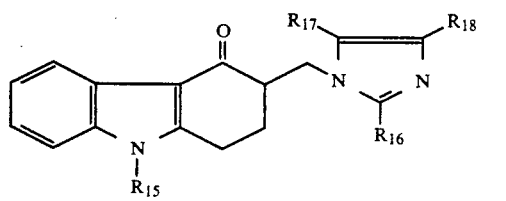

wherein $R_{15}$ is hydrogen, $(C_{1-10})$alkyl, $(C_{3-9})$cycloalkyl, $(C_{3-6})$alkenyl, phenyl or phenyl$(C_{1-3})$alkyl, and one of $R_{16}$, $R_{17}$ or $R_{18}$ is hydrogen, $(C_{1-6})$alkyl, $(C_{3-7})$cycloalkyl, $(C_{2-6})$alkenyl or phenyl$(C_{1-3})$alkyl, and the other substituents are, independently, hydrogen or $(C_{1-4})$alkyl.

5. A composition according to claim 4 wherein the compound of formula Ia is 1,2,3,9-tetrahydro-9-methyl-3-[(2-methyl-1H-imidazol-1-yl)-methyl]-4H-carbazol-4-one.

6. A composition according to claim 4 wherein the opiate is morphine.

7. A composition according to claim 4 in unit dosage form comprising from 0.5 to 1 milligram of a compound of formula Ia.

* * * * *